US00PP31649P2

(12) United States Plant Patent
Caster et al.

(10) Patent No.: US PP31,649 P2
(45) Date of Patent: Apr. 14, 2020

(54) BLUEBERRY PLANT VARIETY NAMED 'DRISBLUEEIGHTEEN'

(50) Latin Name: ***Vaccinium corymbosum* L.**
Varietal Denomination: DrisBlueEighteen

(71) Applicant: Driscoll's, Inc., Watsonville, CA (US)

(72) Inventors: Brian K. Caster, Watsonville, CA (US); Jennifer K. Izzo, Watsonville, CA (US)

(73) Assignee: Driscoll's, Inc., Watsonville, CA (US)

( * ) Notice: Subject to any disclaimer, the term of this patent is extended or adjusted under 35 U.S.C. 154(b) by 0 days.

(21) Appl. No.: 16/350,012

(22) Filed: Sep. 12, 2018

(51) Int. Cl.
*A01H 6/36* (2018.01)
*A01H 5/08* (2018.01)

(52) U.S. Cl.
USPC ..... Plt./157

(58) Field of Classification Search
USPC ..... Plt./156, 157
See application file for complete search history.

(56) References Cited

U.S. PATENT DOCUMENTS

| | | | |
|---|---|---|---|
| PP6,699 | P | 3/1989 | Wood |
| PP11,807 | P2 | 3/2001 | Lyrene |
| PP12,783 | P2 | 7/2002 | Lyrene |
| PP20,436 | P2 | 10/2009 | Caster et al. |
| PP20,449 | P2 | 11/2009 | Caster et al. |
| PP20,488 | P2 | 11/2009 | Caster et al. |
| PP24,407 | P3 | 4/2014 | Caster et al. |
| PP24,489 | P3 | 5/2014 | Caster et al. |
| PP24,568 | P3 | 6/2014 | Caster et al. |
| PP24,569 | P3 | 6/2014 | Caster et al. |
| PP24,605 | P3 | 7/2014 | Caster et al. |
| PP26,287 | P3 | 1/2016 | Caster et al. |
| PP26,451 | P3 | 3/2016 | Caster et al. |
| PP26,537 | P3 | 3/2016 | Caster et al. |
| PP26,643 | P3 | 4/2016 | Caster et al. |
| PP26,748 | P3 | 5/2016 | Caster et al. |
| PP27,622 | P3 | 1/2017 | Caster et al. |
| PP28,933 | P2 | 2/2018 | Caster et al. |

OTHER PUBLICATIONS

Mowrey et al., Unpublished U.S. Appl. No. 16/530,020, filed Sep. 13, 2018, titled "Blueberry Plant Variety Named 'DrisBlueSixteen'".
Caster et al., Unpublished U.S. Appl. No. 16/350,021, filed Sep. 13, 2018, titled "Blueberry Plant Variety Named 'DrisBlueSeventeen'".

*Primary Examiner* — Susan McCormick Ewoldt
*Assistant Examiner* — Karen M Redden
(74) *Attorney, Agent, or Firm* — Morrison & Foerster LLP

(57) ABSTRACT

A new and distinct variety of blueberry plant named 'DrisBlueEighteen', particularly selected for its mid-range chill requirement suitable for production in latitudes ranging from 30 to 40 degrees, its productiveness, as well as its large, firm, sweet-flavored fruit with an attractive appearance, is disclosed.

4 Drawing Sheets

Latin name:

Botanical classification: *Vaccinium corymbosum* L.

Varietal denomination: The varietal denomination of the claimed variety of blueberry plant is 'DrisBlueEighteen'.

BACKGROUND OF THE INVENTION

Blueberry plants are perennial flowering plants with indigo-colored berries from the section *Cyanococcus* within the genus *Vaccinium*. Many commercially sold species with English common names, including blueberry, are currently classified in section *Cyanococcus* of the genus *Vaccinium* and come predominantly from North America. Many North American native species of blueberries are grown commercially in the Southern Hemisphere in Australia, New Zealand, and South American nations.

*Vaccinium corymbosum*, the northern highbush blueberry, is a North American species of blueberry which has become a food crop of significant economic importance. It is native to eastern Canada and the eastern and southern United States, from Ontario east to Nova Scotia and south as far as Florida and eastern Texas. It has been naturalized in Europe, Japan, New Zealand, and the Pacific Northwest of North America. Other common names include blue huckleberry, tall huckleberry, swamp huckleberry, high blueberry, and swamp blueberry.

Blueberries are usually erect, prostrate shrubs that can vary in size from approximately four inches to approximately 13 feet in height. In the commercial production of blueberries, the smaller species are known as "lowbush blueberries", while the larger species are known as "highbush blueberries".

Blueberry bushes typically bear fruit in the middle of the growing season. However, fruiting times can be affected by local conditions such as altitude and latitude. As such, peak crop can vary from May to August in the northern hemisphere, depending upon these conditions.

Blueberries are a popular fruit that is typically consumed as fresh fruit, individually quick frozen (IQF) fruit, or in prepared foods, such as purées, juices, jellies, jams, baked goods, snack foods, and cereals.

Blueberry is an important and valuable fruit crop. Accordingly, there is a need for new varieties of blueberry plant. In particular, there is a need for improved varieties of blueberry plant that are stable, high yielding, and agronomically sound.

SUMMARY OF THE INVENTION

In order to meet these needs, the present invention is directed to an improved variety of blueberry plant. In particular, the invention relates to a new and distinct variety of blueberry plant (*Vaccinium corymobsum* L.), which has been denominated as 'DrisBlueEighteen'.

Blueberry plant variety 'DrisBlueEighteen' was discovered in Santa Cruz County, Calif. in September of 2006 and originated from a cross between the proprietary female parent blueberry plant '136D 2' (unpatented) and the proprietary male parent blueberry plant '181C 1' (unpatented). The original seedling of the new variety was first asexually propagated via cuttings in Santa Cruz County, Calif. in 2008. 'DrisBlueEighteen' was subsequently asexually propagated via cuttings and underwent further testing in Santa Cruz County, Calif. for ten years (2008 to 2017). The present blueberry variety has been found to be stable and reproduce true to type through successive asexual propagations via cuttings.

'DrisBlueEighteen' exhibits the following distinguishing characteristics when grown under normal horticultural practices in Santa Cruz County, Calif.:

1. High yield; and
2. Large fruit size.

The original seedling of the new variety was selected for its mid-range chill requirement suitable for production in latitudes ranging from 30 to 40 degrees, its productiveness, as well as its large, firm, sweet-flavored fruit with an attractive appearance.

BRIEF DESCRIPTION OF THE DRAWINGS

This new blueberry plant variety is illustrated by the accompanying photographs. The colors shown are as true as can be reasonably obtained by conventional photographic procedures. The photographs are of plants that are seven years old.

DETAILED BOTANICAL DESCRIPTION

Figure 1:
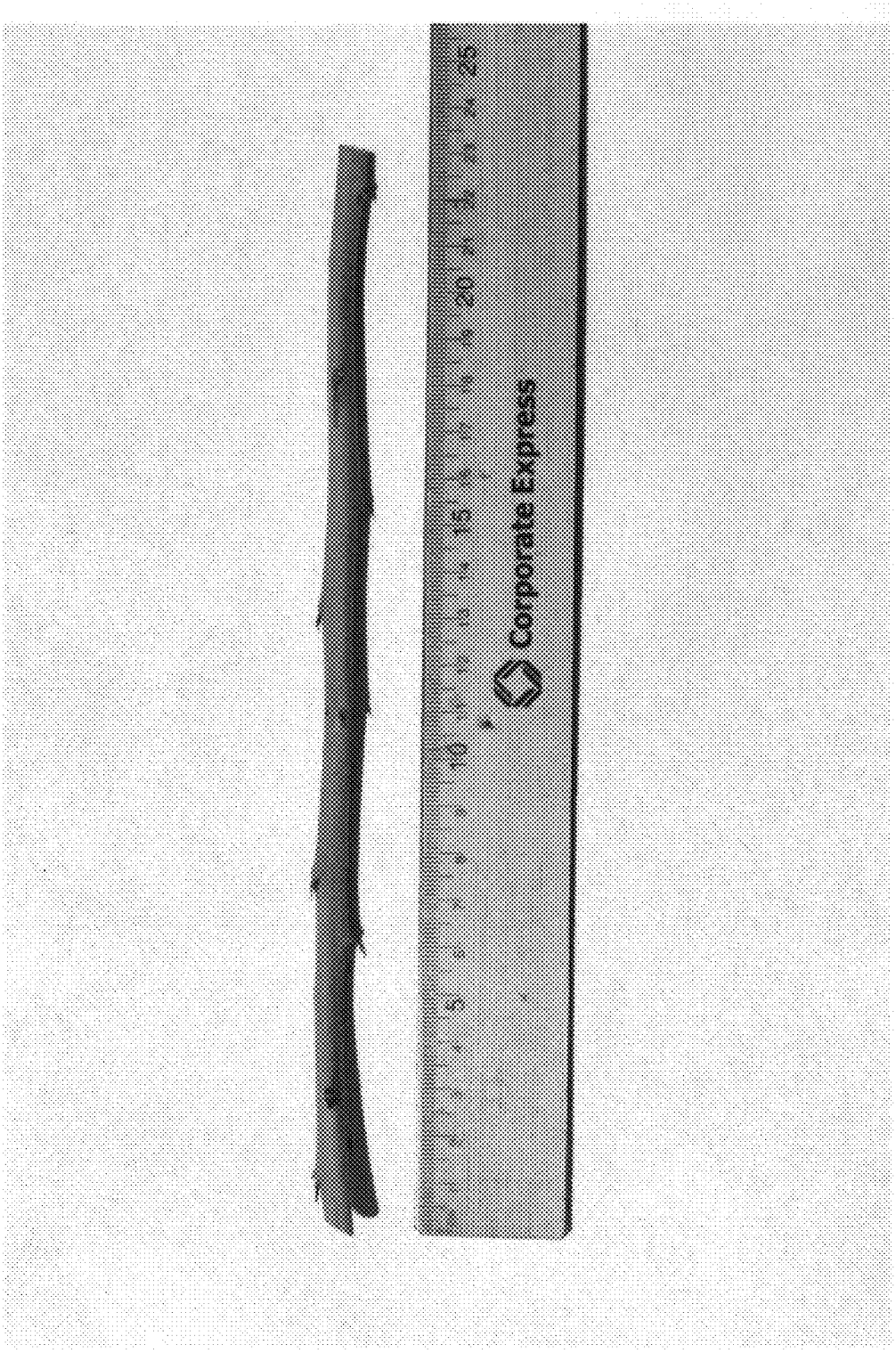
FIG. 1 illustrates a section of a cane of variety 'DrisBlueEighteen'.
Figure 2:
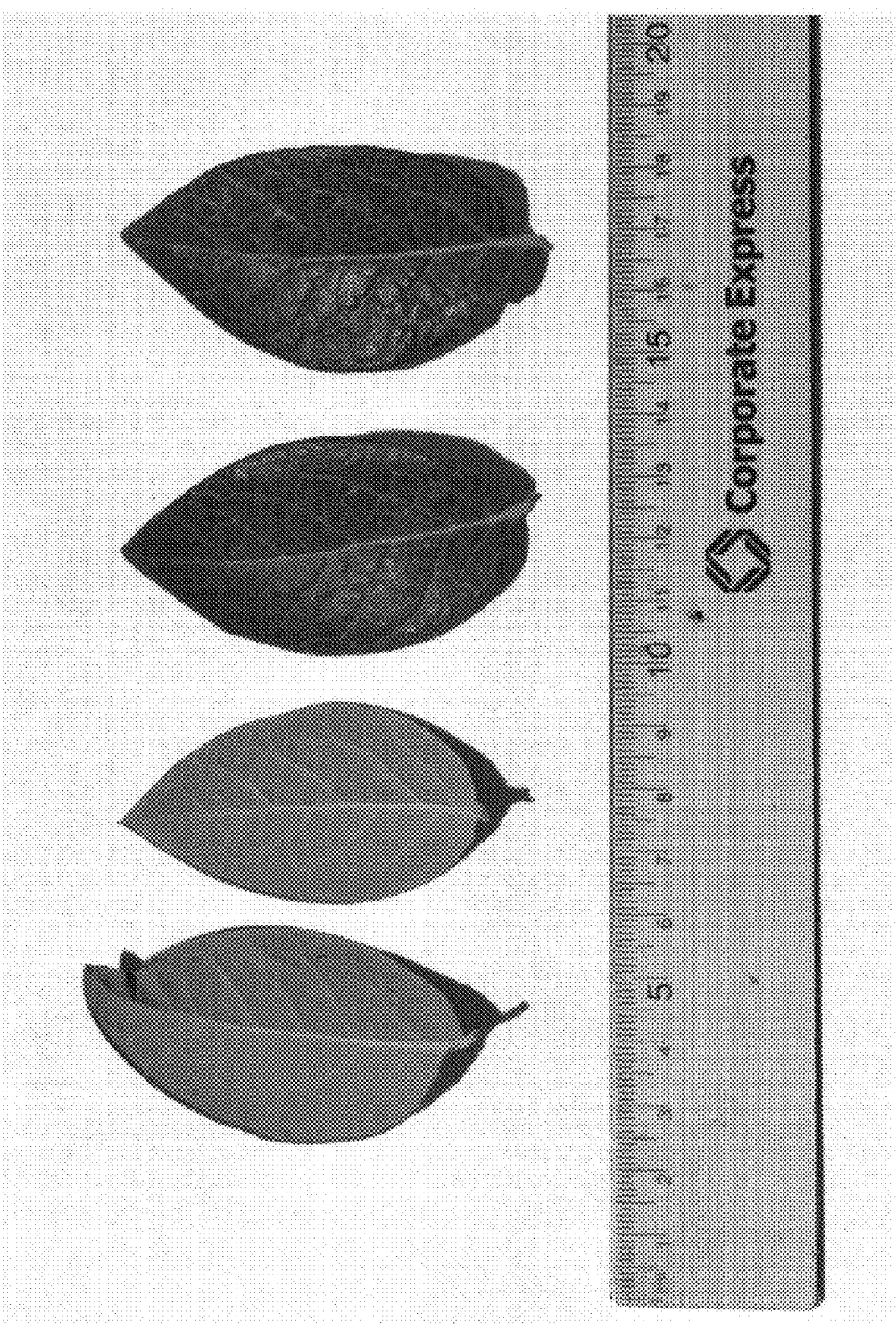
FIG. 2 illustrates leaves of variety 'DrisBlueEighteen'.
Figure 3:
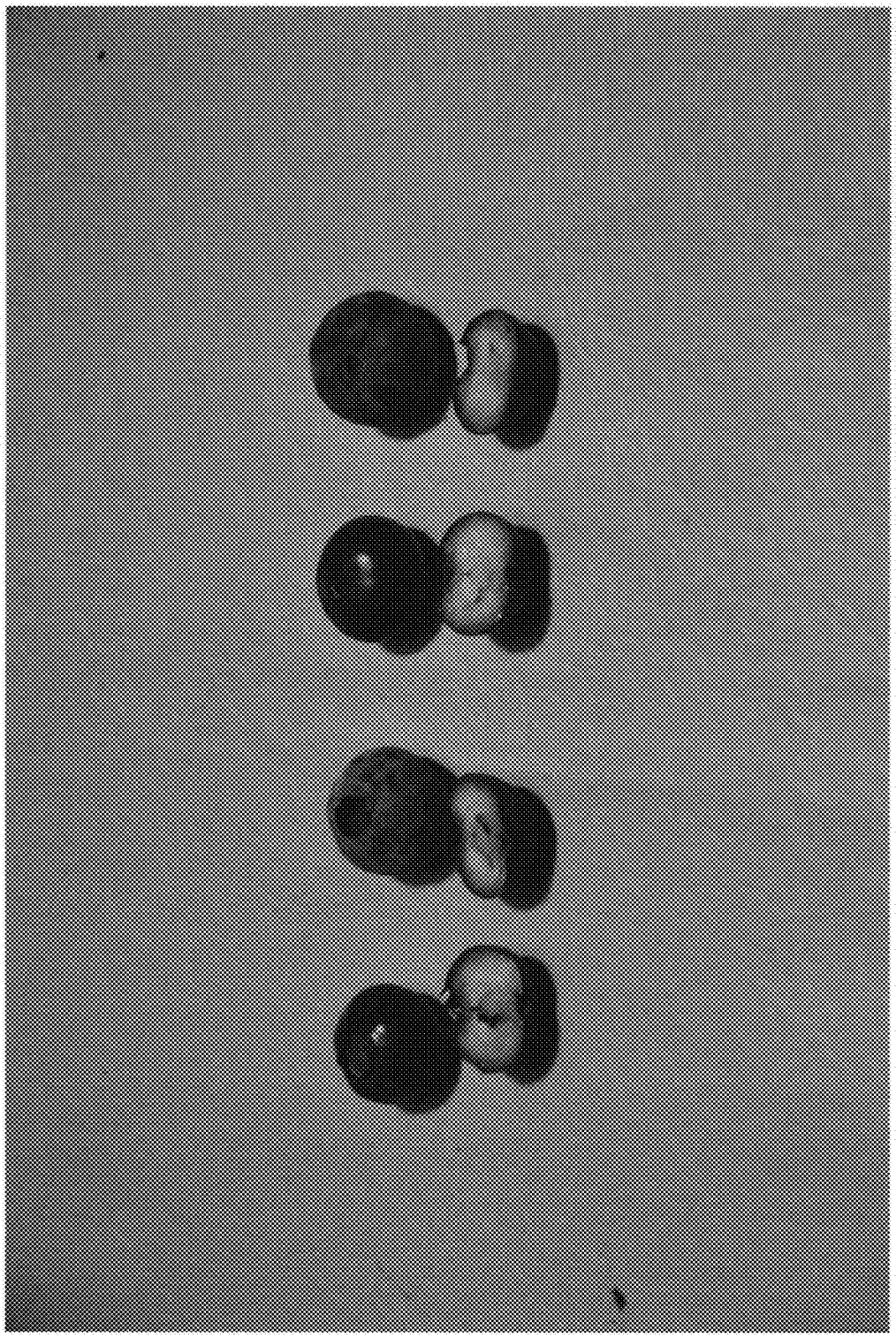
FIG. 3 illustrates whole fruit and cross-sections of the fruit of variety 'DrisBlueEighteen'.
Figure 4:
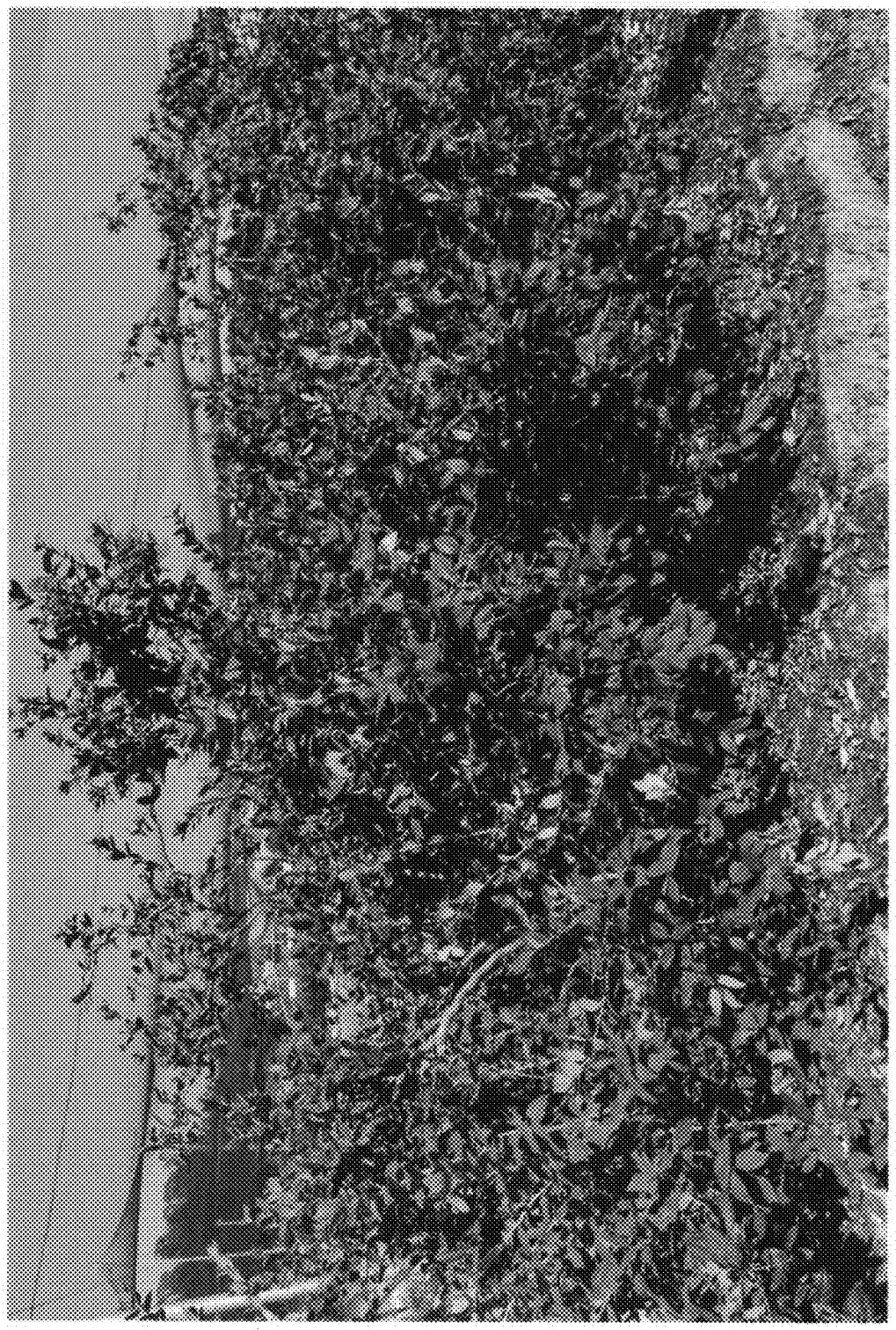
FIG. 4 illustrates plants of variety 'DrisBlueEighteen'.

The following description sets forth the distinctive characteristics of 'DrisBlueEighteen'. The data which define these characteristics is based on observations taken in Santa Cruz County, Calif. from 2008 to 2017. This description is in accordance with UPOV terminology. Color designations, color descriptions, and other phenotypical descriptions may deviate from the stated values and descriptions depending upon variation in environmental, seasonal, climatic and cultural conditions. 'DrisBlueEighteen' has not been observed under all possible environmental conditions. The botanical description of 'DrisBlueEighteen' was taken from 7-year-old plants, unless indicated otherwise. The indicated values represent averages calculated from measurements of several plants. Color references are primarily to The R.H.S. Colour Chart of The Royal Horticultural Society of London (R.H.S.) (2007 edition). Descriptive terminology follows the *Plant Identification Terminology, An Illustrated Glossary,* 2$^{nd}$ edition by James G. Harris and Melinda Woolf Harris, unless where otherwise defined.

Classification:

*Family*.—Ericaceae.

*Botanical*.—*Vaccinium corymbosum* L.

*Common name*.—Blueberry.

*Variety name*.—'DrisBlueEighteen'.

Parentage:

*Female parent*.—The proprietary blueberry plant '136D 2'.

*Male parent*.—The proprietary blueberry plant '181C 1'.

Plant:

*Height*.—187.0 cm.

*Width*.—212.0 cm.

*Length/width ratio*.—0.9.

*Growth habit*.—Semi-upright.

*One-year-old canes* (*young canes*).—Length: 71 cm. Diameter at the base: 6 mm. Diameter at the tip: 1 mm. Internode length on the upper half: 15.5 mm. Color: RHS 145A (Yellow-green). One-year-old cane texture: Smooth.

*Five-year-old canes* (*mature canes*).—Length: 68 cm. Diameter at the base: 26 mm. Diameter at the tip: 6 mm. Five-year-old cane texture: Rough. Five-year-old cane color: RHS 199C (Greyed brown).

*Flower bud anthocyanin color*.—RHS 60C (Strong purplish red).

Leaves:

*Length*.—59.8 mm.

*Width*.—29.3 mm.

*Length/width ratio*.—2.0.

*Internode length*.—15.47 mm.

*Shape*.—Lanceolate.

*Margin*.—Entire.

*Color on upper side*.—RHS 139A (Green).

*Leaf arrangement*.—Alternate.

*Leaf venation pattern*.—Reticulate.

*Leaf vein color*.—RHS 152D (Dark greenish yellow).

*Shape of the leaf apex*.—Cuspidate.

*Shape of the leaf base*.—Cuneate.

*Leaflet texture of upper side*.—Smooth.

*Leaflet texture of lower side*.—Smooth.

*Leaflet color of lower side*.—RHS 191A (Greyed-green).

*Petiole*.—Length: 2.9 mm. Diameter: 2.10 mm. Petiole texture: Slightly pubescent. Petiole color: RHS 144B (Yellow-green).

Flowers:

*Length* (*excluding peduncle*).—11.14 mm.

*Diameter*.—7.01 mm.

*Length/width ratio*.—1.6.

*Presence of flower fragrance*.—Absent.

*Flower bud*.—Length: 7 mm. Width: 3 mm. Number of flowers per bud: 5.

*Pedicel*.—Length: 3.24 mm. Diameter: 0.99 mm. Pedicel color: RHS 145A (Strong yellow-green).

*Corolla*.—Shape: Urceolate. Anthocyanin color of corolla tube: RHS N57C (Deep purplish pink). Ridges on tube: Present. Petal width (ridge to ridge): 3.53 mm. Petal color: RHS 157B (Pale yellow-green). Diameter of corolla aperture: 3.36 mm.

*Reproductive organs*.—Style length (including stigma): 8.06 mm. Ovary color: RHS 191B (Greyish yellow-green). Anther color: RHS N172D (Moderate orange). Pollen color: RHS 4D (Pale yellow-green).

*Flowering interval on one-year shoot*.—March to April.

*Pollinator requirement*.—Insect pollinators such as honeybees or bumblebees are recommended.

Fruit:

*Length*.—13.13 mm.

*Diameter*.—17.63 mm.

*Length/width ratio*.—0.7.

*Shape in longitudinal sections*.—Round.

*Attitude of sepals*.—Erect to semi-erect.

*Type of sepals*.—Straight.

*Calyx basin*.—Diameter: 6.69 mm. Depth: 2.45 mm. Diameter/depth ratio: 2.7.

*Weight*.—3.0 g.

*Number of berries per cluster*.—3.70.

*Peduncle length*.—17.70 mm.

*Diameter of pedicel*.—0.88 mm.

*Seed*.—Length: 1.73 mm. Width: 0.87 mm. Length/width ratio: 2.0. Seed color: RHS N167A (Brownish orange).

*Color of unripe fruit*.—RHS 144B (Strong yellow-green).

*Color of skin* (*after removal of bloom*).—RHS 103A (Greyish purplish blue).

*Color of flesh*.—RHS 145C (Light yellow-green).

*Fruit firmness*.—Firm.

*Fruiting type*.—On one-year-old shoots.

*Ripening interval on one-year-old shoot*.—June to July.

*Approximate date of first fruit pick*.—June 1.

*Approximate date of last fruit pick*.—August 15.

*Market use of fruit*.—Fresh market.

*Shipping and storage characteristics*.—Following harvest, fruit have been stored for 21 days when maintained under cooled temperatures that are standard for blueberry storage.

*Yield*.—8000 kg/hectare to 12,000 kg/hectare of fruit per season from 60-month-old plants when grown in Santa Cruz County, Calif.

Resistance to abiotic stress, pests, and diseases:

*Heat*.—Moderately susceptible.

*Spotted-wing drosophila* (*drosophila suzukii*).—Moderately susceptible.

*Botrytis fruit rot* (*botrytis cinerea*).—Moderately resistant.

*Botryosphaeria stem blight*.—Moderately susceptible.

*Phomopsis stem blight*.—Moderately susceptible.

COMPARISONS TO PARENTAL AND COMMERCIAL BLUEBERRY VARIETIES

'DrisBlueEighteen' differs from the proprietary female parent '136D 2' (unpatented) in that 'DrisBlueEighteen' has higher yield in a concentrated ripening period when compared to '136D 2'.

'DrisBlueEighteen' differs from the proprietary male parent '181C 1' (unpatented) in that fruit of 'DrisBlueEighteen' are larger in size than fruit of '181C 1'.

'DrisBlueEighteen' differs from commercial blueberry plant variety 'DrisBlueOne' (U.S. Plant Pat. No. 20,449) in that fruit of 'DrisBlueEighteen' are larger in size than fruit of 'DrisBlueOne'. Additionally, plants of 'DrisBlueEighteen' have a more upright plant architecture than plants of 'DrisBlueOne'.

'DrisBlueEighteen' differs from commercial blueberry plant variety 'Legacy' (unpatented) in that 'DrisBlueEighteen' yields earlier than 'Legacy'. Additionally, fruit of 'DrisBlueEighteen' are larger in size than fruit of 'Legacy'.

What is claimed is:

1. A new and distinct variety of blueberry plant designated 'DrisBlueEighteen' as shown and described herein.

* * * * *